United States Patent [19]
Zebuhr

[11] Patent Number: 5,769,102
[45] Date of Patent: *Jun. 23, 1998

[54] AUTOMATED DENTAL CLEANER

[75] Inventor: William H. Zebuhr, Nashua, N.H.

[73] Assignee: DynaProducts, Inc., Nashua, N.H.

[ * ] Notice: The term of this patent shall not extend beyond the expiration date of Pat. No. 5,647,385.

[21] Appl. No.: 620,038

[22] Filed: Mar. 21, 1996

Related U.S. Application Data

[63] Continuation-in-part of Ser. No. 418,837, Apr. 7, 1995, Pat. No. 5,647,385.

[51] Int. Cl.$^6$ .................................................. A61C 15/00
[52] U.S. Cl. ........................ 132/322; 132/323; 132/324; 132/325; 132/327; 15/22.1; 15/22.2; 15/167.2
[58] Field of Search .................................. 132/322, 323, 132/324, 325, 326, 327, 328, 329; 15/4, 22.1, 22.2, 167.2

[56] References Cited

U.S. PATENT DOCUMENTS

| | | | |
|---|---|---|---|
| 2,467,221 | 4/1949 | Pastl ......................................... | 132/92 |
| 3,421,524 | 1/1969 | Waters ..................................... | 132/92 |
| 3,534,745 | 10/1970 | Waters ..................................... | 132/92 |
| 3,667,483 | 6/1972 | McCabe ................................... | 132/92 |
| 3,759,274 | 9/1973 | Warner .................................. | 132/92 R |
| 3,799,177 | 3/1974 | Bragg ..................................... | 132/92 |
| 3,847,167 | 11/1974 | Brien ................................... | 132/92 R |
| 3,847,168 | 11/1974 | Schlegel .............................. | 132/92 R |
| 3,886,956 | 6/1975 | Cash ....................................... | 132/91 |
| 4,014,354 | 3/1977 | Garrett ................................... | 132/90 |
| 4,235,253 | 11/1980 | Moore ................................. | 132/92 R |
| 4,245,658 | 1/1981 | Lecouturier .......................... | 132/92 A |
| 4,307,740 | 12/1981 | Florindez et al. ................... | 132/92 R |
| 4,326,549 | 4/1982 | Hinding ............................. | 132/92 R |
| 4,338,957 | 7/1982 | Meibauer ................................ | 132/91 |
| 4,458,702 | 7/1984 | Grollimund .......................... | 132/92 A |
| 4,586,521 | 5/1986 | Urso ..................................... | 132/92 R |
| 4,605,025 | 8/1986 | McSpadden ........................ | 132/92 R |
| 4,706,695 | 11/1987 | Urso ................................... | 132/92 R |
| 4,880,382 | 11/1989 | Moret et al. ........................... | 433/118 |
| 5,000,684 | 3/1991 | Odrich ................................ | 433/125 |
| 5,016,660 | 5/1991 | Boggs .................................. | 132/322 |
| 5,069,233 | 12/1991 | Ritter .................................... | 132/322 |
| 5,085,236 | 2/1992 | Odneal et al. ........................ | 132/322 |
| 5,170,809 | 12/1992 | Imai et al. ............................ | 132/322 |
| 5,176,157 | 1/1993 | Mazza .................................. | 132/322 |
| 5,207,773 | 5/1993 | Henderson ............................ | 132/322 |
| 5,217,031 | 6/1993 | Santoro ................................ | 132/322 |
| 5,323,796 | 6/1994 | Urso ..................................... | 132/322 |
| 5,606,984 | 3/1997 | Gao ...................................... | 132/322 |

OTHER PUBLICATIONS

Sales brochure by Oralgiene, "A Scientific Breakthrough in Dental Hygiene", at least by Dec., 1995.

*Primary Examiner*—Gene Mancene
*Assistant Examiner*—Pedro Philogene
*Attorney, Agent, or Firm*—Brooks & Kushman P.C.

[57] ABSTRACT

An automated dental cleaner (320) comprises a subassembly (324) having a pair of pivotally supported spaced tines (336) for supporting a movable floss span (338) therebetween. A pair of capstans (346, 352) are provided for drivingly reciprocating the floss span. Floss supply and take-up spools (340, 342) are arranged for continuously replacing the span. A main assembly (322) includes a housing containing a motor-driven multi-function transmission for driving the capstans and take-up spool, and for reciprocating the tines vertically. The main assembly and the subassembly are detachably connectable to each other for expedient replacement of the subassembly by a user. An additional feature on each tine includes a bracing pad (424) shaped for bracing the fork on teeth and gums. Brush bristles (426, 428) added to the tines help to inhibit fork lateral motion and enable the cleaner to floss and brush teeth simultaneously.

15 Claims, 14 Drawing Sheets

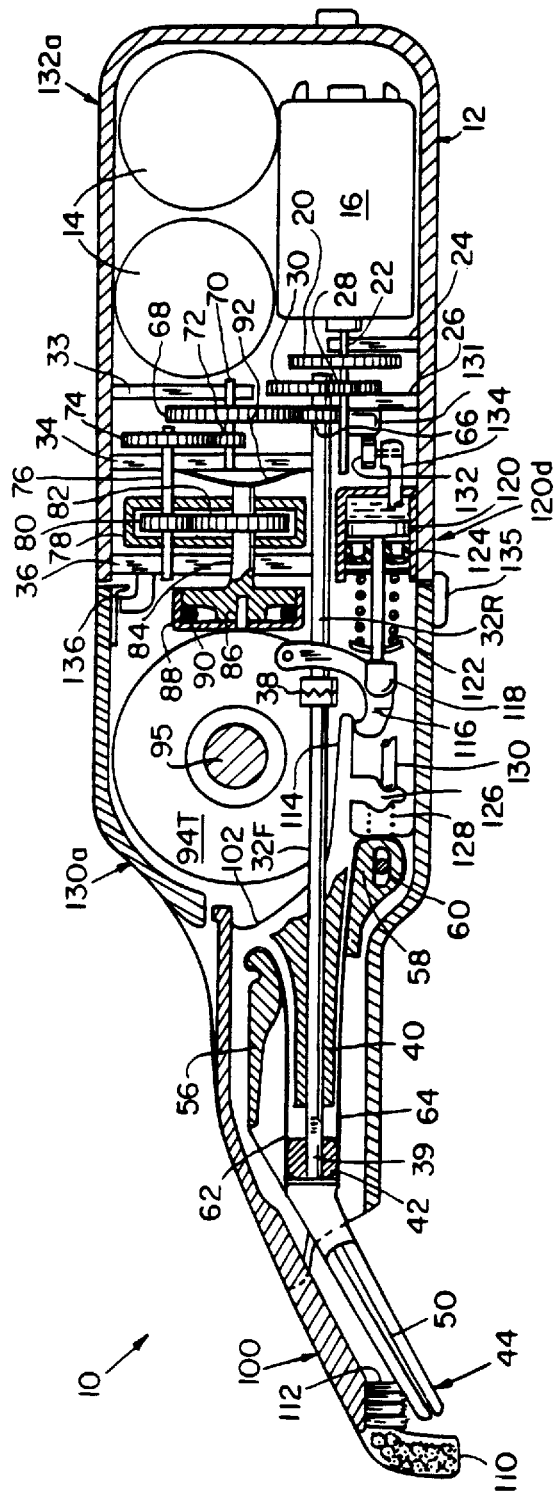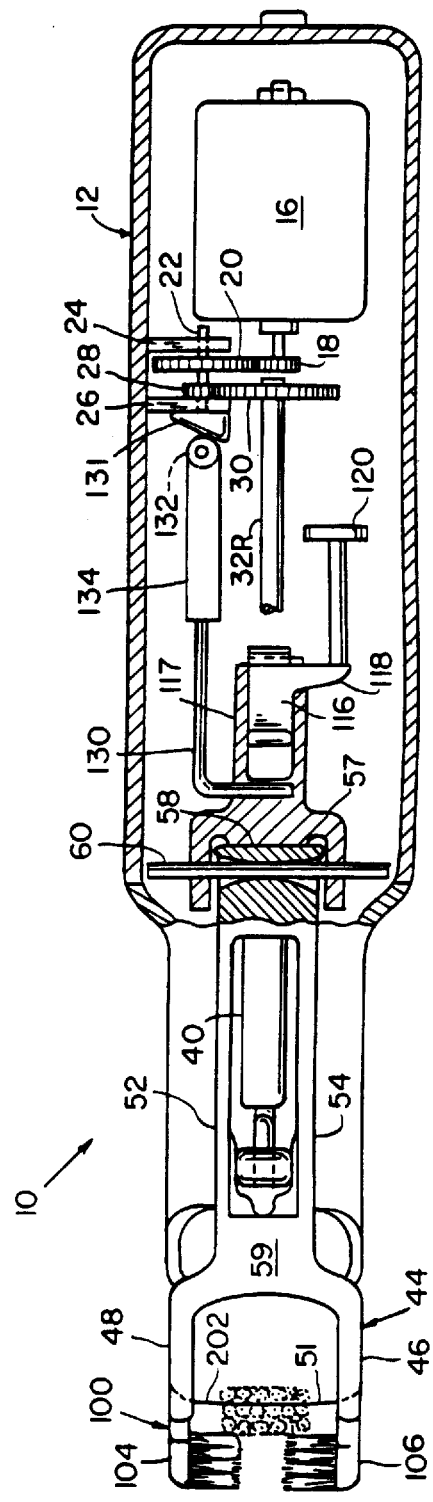

AUTOMATED DENTAL CLEANER

RELATED APPLICATION

This application is a continuation-in-part of U.S. patent application No. 08/418,837 filed on Apr. 7, 1995 which is incorporated herein by reference in its entirety, now U.S. Pat. No. 5,647,385.

BACKGROUND

Most adults have some degree of gum disease. In an advanced form, the ailment accounts for about three quarters of lost teeth. Unhealthy gums can also lead to other health problems including serious infections.

Disease of the gums can be avoided by removal of plaque, especially from under the gum line. Brushing, alone, is not sufficient because it does not clean under the gum line between teeth. Consumer organizations have tested the available plaque removing products, including the high tech powered brushes. They report that the most important aspect of proper dental hygiene is flossing.

Proper flossing by hand, however, is an arduous and loathsome regimen. It requires dexterity and some degree of skill to properly manipulate the floss to clean all the interdental surfaces down to the attached gingiva. Dexterous people find flossing tedious and it is exceedingly difficult for the nondexterous. Consequently, an estimated 90 percent of adults have some degree of the disease in spite of efforts by their dentists to teach them how to floss.

An automated dental cleaner is, therefore, needed to reduce the amount of tedious work, perseverance, and dexterity required for proper flossing and brushing.

SUMMARY OF THE INVENTION

The present invention provides a dental cleaner including a fork having a pair of spaced tines for supporting a span of dental floss extending therebetween. First and second brushes attached to the tines have bristles extending inward between the tines for simultaneously engaging lingual and buccal tooth surfaces, thereby brushing and flossing the teeth at the same time.

In preferred embodiments, the brushes have bristles of differing lengths and the floss span and the brushes are driven by a drive.

The present invention also provides a dental cleaner including a frame supporting a pair of spaced tines. The tines support a moveable span of dental floss therebetween and have guides for guiding the transfer of dental floss from one tine to the other tine. A drive reciprocates the floss span between the tines to floss teeth.

In one embodiment, a pair of bracing pads are included on an inner side of a respective tine. Each pad has a surface facing the other pad which extends down and away from the other pad to conform to a user gum line, thereby comfortably bracing the tines thereon when flossing.

In another embodiment, the frame and tines are part of a subassembly. Additionally, a pair of capstans near the tines engage and drive the floss to reciprocate the floss span. A floss supply and take-up system replaces used floss in the floss span with fresh floss. A main assembly is included and has a housing which contains the drive for driving the capstans. The drive also reciprocates the tines transverse to the floss span. The main assembly and the subassembly are detachably connectable to each other. The subassembly is preferably a disposable cartridge which is replaced after all the dental floss is used. The capstans as well as the floss supply and take-up system include parallel support shafts. The parallel shafts allow the subassembly to be easily connected to and disconnected from the main assembly.

A preferred drive for the dental cleaner includes a forward capstan gear for driving a forward capstan and a reverse capstan gear for driving a reverse capstan. The forward and reverse capstans drive floss between the tines. A drive rack moves in a path to alternately drive the forward capstan gear and the reverse capstan gear.

In preferred embodiments, the drive further comprises an intermediate gear which drives the reverse capstan gear. The intermediate gear is driven by the drive rack. The forward capstan gear, the reverse capstan gear and the intermediate gear are sized to produce a gear ratio such that when driven by the drive rack, the forward capstan gear rotates a greater amount than the reverse capstan gear. This allows used floss to be replaced with fresh floss.

First and second protrusions on the drive rack engage and position the forward capstan gear and the intermediate gear into the proper orientation for engaging the drive rack. A crank is coupled to the drive rack for reciprocating the drive rack. A joint on the drive rack permits both reciprocal motion of the drive rack and pivotal motion of the drive rack. The drive rack pivots to alternately engage the forward capstan gear and the intermediate gear. The joint preferably comprises a cam for guiding the drive rack. The drive rack has a first surface with teeth for engaging the forward capstan gear and a second surface with teeth on an opposite side of the drive rack for engaging the intermediate gear.

A floss supply spool supplies floss to the tines and a floss take-up spool receives used floss from the tines. A supply spool spring is coupled to the floss supply spool for creating tension in the floss supplied by the floss supply spool to the tines. A take-up spool spring is coupled to the floss take-up spool for creating tension in the floss received by the floss take-up spool from the tines.

The present invention also provides a bite device for driving a span of floss supported between spaced tines of a fork of a dental cleaner through a tight interdental gap. A bite surface is supported by the fork and spaced apart from the span of floss. The bite surface is capable of being bitten by a tooth opposite to the interdental gap to drive the span of floss through the interdental gap.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale.

FIG. 2 is a side view, in section, of the dental cleaner of FIG. 1.

FIG. 3 is a bottom view, partly in section, of the dental cleaner of FIG. 1 with some parts removed.

DETAILED DESCRIPTION OF THE PREFERRED EMBODIMENTS

Figure 1:
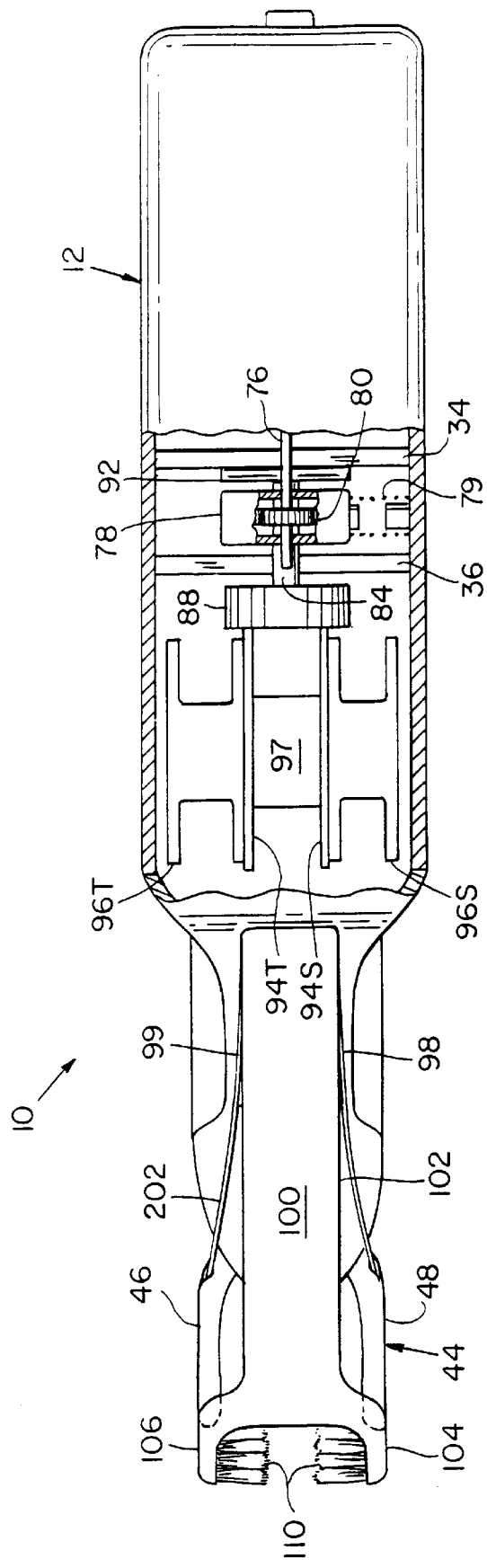
FIG. 1 is a top view, partly in section, of a preferred embodiment of an automated dental cleaner constructed in accordance with the invention with some parts removed for clarity.
Figure 4:
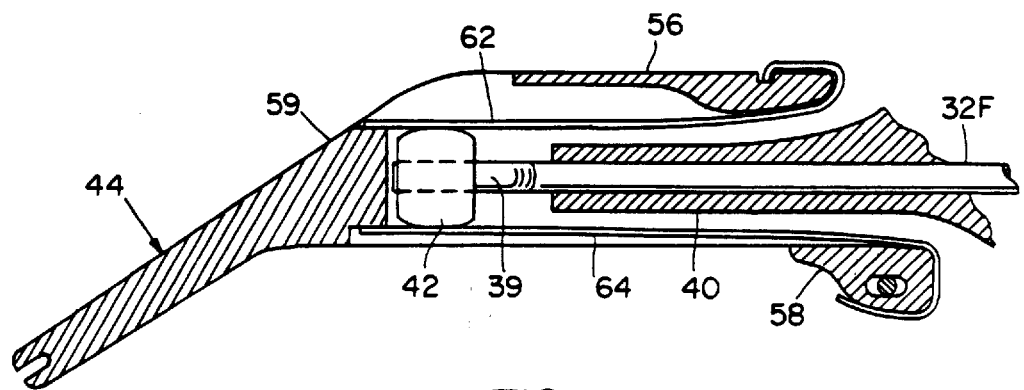
FIG. 4 is an expanded fragmental side view, in section, of the cleaner of FIG. 1 showing the flossing fork with leaf springs engaged by a roller on a crank that reciprocates the fork.
Figure 5:
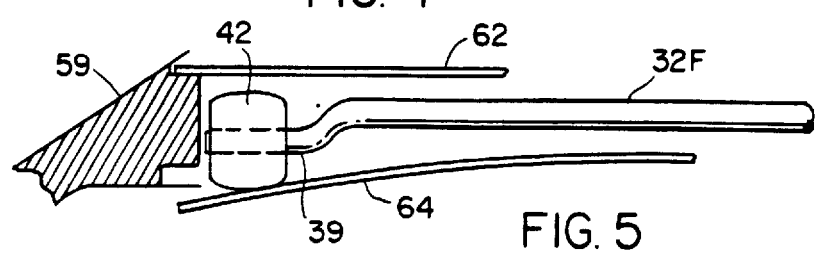
FIG. 5 is the view of FIG. 4, further fragmented, showing the crank and roller in a different position and one of the leaf springs yielding as the flossing fork encounters resistance.

A preferred embodiment of an automated dental cleaner embodying the principles of the present invention is shown in FIGS. 1–7 and is identified generally by reference numeral 10. Dental cleaner 10 comprises a hollow elongated housing 12 which encloses two rechargeable batteries 14 (FIG. 2). Conventional electrical connecting means (not shown) connects the batteries for energizing an electric motor 16 to drive the dental cleaner. A conventional electrical switch (not shown) is included in the connecting means for actuating the motor.

A plurality of systems operate various working features of dental cleaner 10. For organization and clarity, each system is separately described hereinafter.

The first system of dental cleaner 10 to be described is the flossing fork system. Fixedly connected to the motor drive shaft is a pinion 18 (FIG. 3) which is drivingly engaged with a driven gear 20. Gear 20 (FIGS. 2 and 3) is coaxially fixed to an axle 22 which is rotatably supported by bearings 24 and 26. Both bearings are fixed to the housing 12.

A pinion 28, coaxially fixed on axle 22, is drivingly engaged with a driven gear 30 which is coaxially fixed to a rear section of a drive shaft 32R. Shaft section 32R is rotatably supported by bearings 34 and 36 which are fixed to housing 12. The shaft includes a front section 32F rotatably supported by a bearing 40 which is fixed in a narrow front end portion of housing 12. Shaft sections 32F and 32R are coaxially connected by a clutch 38. A front end portion of shaft section 32F is offset from the main shaft (best seen in FIG. 5) to form a crank 39. A roller 42 is rotatably supported on the crank.

Movably attached to a front end portion of housing 12 is a flossing fork 44 (FIGS. 1–5) having a pair of spaced flossing tines 46 and 48 for receiving teeth to be cleaned therebetween. The tines extend frontward and downward at a slight angle. An outer side of each tine includes a groove 50 (best seen in FIG. 2) which extends longitudinally along the tine and around the distal end portion thereof. The grooves serve as guides for receiving and guiding floss therein. Thus, floss 202 can extend along each tine to span from one tine to the other tine at their distal end portions, thereby forming a floss span 51 between the tines.

A trunk portion of the flossing fork 44 includes spaced opposed side walls 52 and 54 (FIG. 3) which are connected by an upper bridge 56 (FIGS. 2 and 4) and a lower bridge 58. A frontal bridge 59 (FIG. 3) connects walls 52, 54 with the fork tines.

The flossing fork 44 is connected between opposed walls of a U-shaped holder 57 (FIG. 3) by a fork pin 60 received in aligned apertures which pass transversely through the holder and through bridge 58. The aperture through bridge 58 is of oblong cross-section at its outer ends, but narrows to an approximately circular cross-section medially. This allows the distal ends of the flossing fork tines to move in an orbital path.

An elongated upper leaf spring 62 (FIGS. 2, 4 and 5) has a rear end portion fixed to bridge 56. A front end portion of spring 62 rests under tension on the top of bridge 59. An elongated lower leaf spring 64 has a rear end portion fixed to bridge 58. A front end portion of spring 64 rests under tension on the bottom of bridge 59.

Received between and engaging the fork walls 52, 54 and leaf springs 62, 64 is roller 42. When motor 16 is energized, the speed reduction gears drive the crank wherein the crank roller 42 reciprocates flossing fork 44 in an orbital path. The fork being compelled to move in the manner of a second class lever.

If floss span 51 encounters resistance, such as a tight gap between adjacent teeth, the tensioned leaf springs 62, 64 yield vertically to the crank roller. This alters the orbital path of the fork to flatten to a linear side to side motion, thereby allowing the floss span to "saw" its way through the tight gap.

The spool operating system of dental cleaner 10 is as follows. A pinion 66 (FIG. 2), coaxially fixed to shaft 32R, drivingly engages a driven gear 68. The gear 68 is coaxially fixed to an axle 70 rotatably supported on bearings 33 and 34. Coaxially fixed to axle 70 is a pinion 72 which is drivingly engaged with a driven gear 74. The gear 74 is coaxially fixed to an axle 76 rotatably supported on bearings 34 and 36.

Pivotally supported on axle 76 is a transmission case 78 having a first set of aligned apertures which receive the axle therethrough. Case 78 includes a second set of aligned apertures which receive a platen drive shaft 84 which passes through the case. Within case 78 is a pinion 80 coaxially fixed to axle 76. Pinion 80 is drivingly engaged with a driven gear 82 which is within the case and coaxially fixed to shaft 84.

A compression spring 79 (FIG. 1) is positioned between case 78 and housing 12. A nodule projecting from the case is received in an end portion of the spring to keep the same in position. The action of spring 79 is to urge case 78 to pivot about axle 76. That action is opposed by torque urging case 78 to pivot in the opposite direction about axle 76 by the gears when the system is driven. The purpose of the pivoting transmission is explained hereinafter.

As shown in FIG. 2, an end of shaft 84 is coaxially fixed to a platen piston 86 which is housed within a drum-shaped platen 88. An O-ring is positioned between the piston and an annular front plate of the platen. The opposite end of shaft 84 is engaged by the crest of an arcuate leaf spring 92 having end portions fixed to bearing 34.

First and second disks 94S and 94T, respectively, (FIGS. 1 and 2) are rotatably supported to rotate independently of each other on an arbor 95. The arbor is supported by a spool support 97 (FIG. 1) which is fixed to housing 12.

A floss supply spool 96S and a floss take-up spool 96T are rotatably supported on arbor 95 and are detachably fixed to the disks, respectively. Conventional spool holding means such as spring-loaded catches (not shown) allow the spools to be quickly snapped on or off by a user. Being attached to a disk, each spool and its associated disk rotate in unison but independently of the other spool and its associated disk.

Platen 88 drivingly engages both disks (best seen in FIG. 1) and is resiliently urged against the disk rims by spring 92. O-ring 90 evens the contact pressure of the platen on the two disks. When motor 16 is energized, the spools will rotate in opposite directions relative to each other.

Floss 202 from the supply spool 96S may be threaded along guide groove 98 and through the guide groove of each flossing fork tine to form the floss span 51. The floss 202 returns along guide groove 99 to take-up spool 96T. Hence, when the spools are driven, the floss span 51 is continuously replaced.

The platen serves as a drive wheel with a rotational axis which is movable relative to each disk while the wheel is drivingly engaged with both disks. The rotation ratio between the wheel and each disk is changeable and consequently the rotation ratio between the supply and take-up spools is changeable.

As floss builds up in take-up spool, the floss in the supply spool is reduced. To keep the tension of floss span 51 and its replacement rate constant, the rate at which the two spools is rotated relative to each other requires continuous change. This is due to the changing radii of the wound floss 202 stored on the spools. Under the described conditions, as said radii change, the relative drive resistance of the disks changes accordingly. Hence, a resultant pivotal torque is induced on transmission case 78 in response to the differing resistance of the two disks. When the system is driven, case 78 (and platen 88) will pivot to the position of least resistance. The disk with the spool having the least amount of floss will be engaged further from the platen center than the other disk. Thus, the spool with the least floss will rotate relatively faster than the other spool. As the relative resistance of the disks changes, the transmission case and platen change position accordingly to maintain constant tension and replacement rate of floss span 51.

The bracing/brushing fork system and damping system of dental cleaner 10 is as follows. Movably mounted to a front end portion of housing 12, above flossing fork 44, is a bracing and brushing fork 100 hereinafter referred to as the BB fork (FIGS. 1–3). As shown in the figures, the BB fork 100 comprises a trunk portion 102 having tines 104 and 106 extending frontward and at a slight angle downward therefrom. Extending inward from each tine are brush bristles 110. Extending downward from a medial position at a frontal end portion of trunk 102 is another set of brush bristles 112.

A rear end portion of trunk 102 includes a pair of lugs 108 (FIGS. 6 and 7) extending downward therefrom. Lugs 108 straddle bridge 58 of the flossing fork and each lug includes an oblong aperture aligned with that of bridge 58 to receive pin 60. Hence, the flossing fork and BB fork are movably supported by the same pin wherein the oblong apertures allow forward and back reciprocating movement of the BB fork 100.

Projecting rearward from a rear end portion of trunk 102 (FIG. 2) is a cantilever 114 slidably engaging the lower end of a damper hook 116. The hook is pivotally supported at an upper end portion by a pin fixedly extending from housing 12. Pivotal motion of the hook is guided at a lower portion thereof by U-shaped guide 117 (FIG. 3) molded onto the floor of housing 12.

Extending laterally from the lower portion of the damper hook 116 is a damper lever 118 which is engaged with a rod fixed to the piston 120 of a damper 120d. Also included in the damper 120d is a return spring 122 (FIG. 2) and a fluid seal 124. Other components of the damper 120d are conventional and are not shown.

Figure 6:
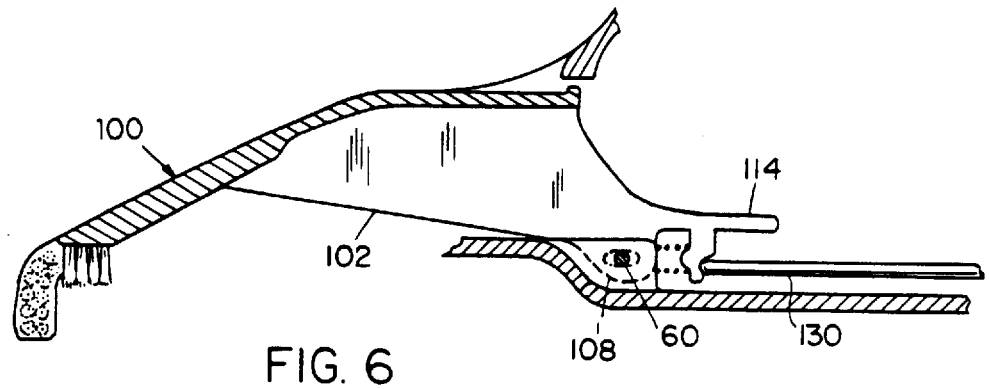
FIG. 6 is a fragmental side view, in section, of the dental cleaner of FIG. 1 showing the bracing and brushing fork connected to the cleaner housing and engaged by a push rod that drives the fork.
Figure 7:
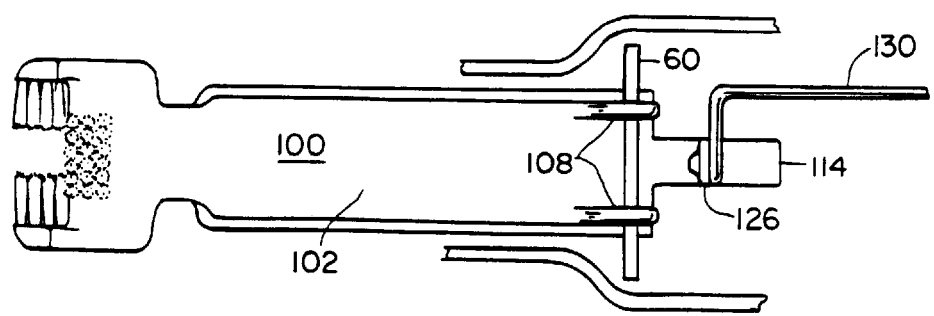
FIG. 7 is a fragmental bottom view, partly in section, of the dental cleaner of FIG. 1 showing the bracing and brushing fork connected to the cleaner housing and engaged by the push rod that drives the fork.
Figure 8:
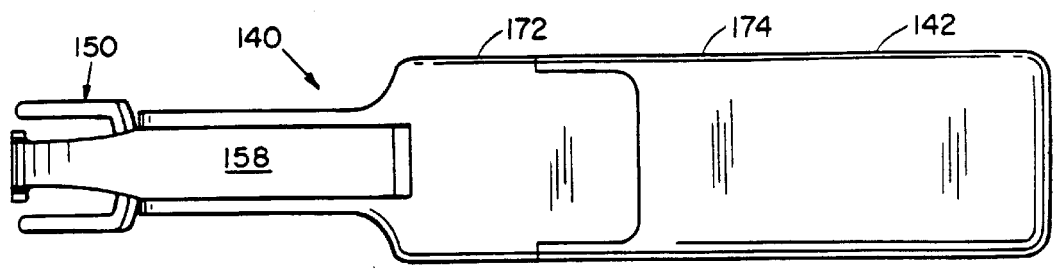
FIG. 8 is a top view of another preferred dental cleaner.
Figure 9:
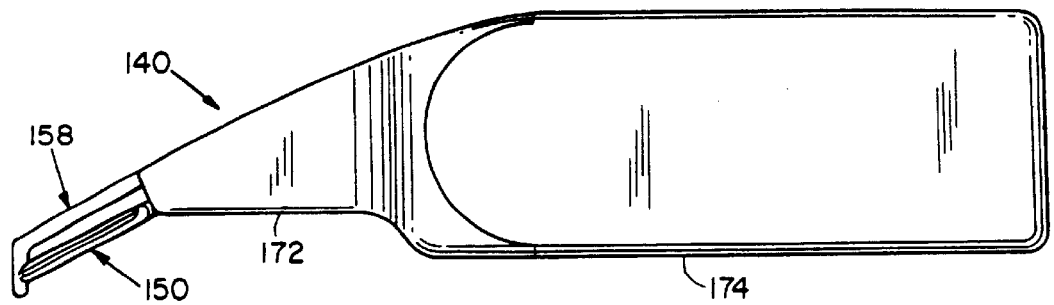
FIG. 9 is a side view of the dental cleaner of FIG. 8.
Figure 11:
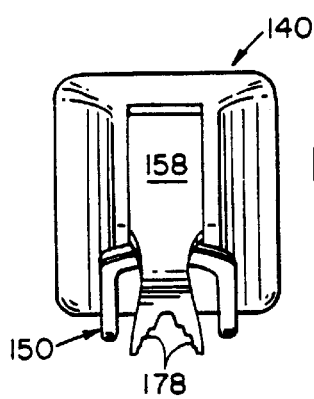
FIG. 11 is a front view of the dental cleaner of FIG. 8.
Figure 10:
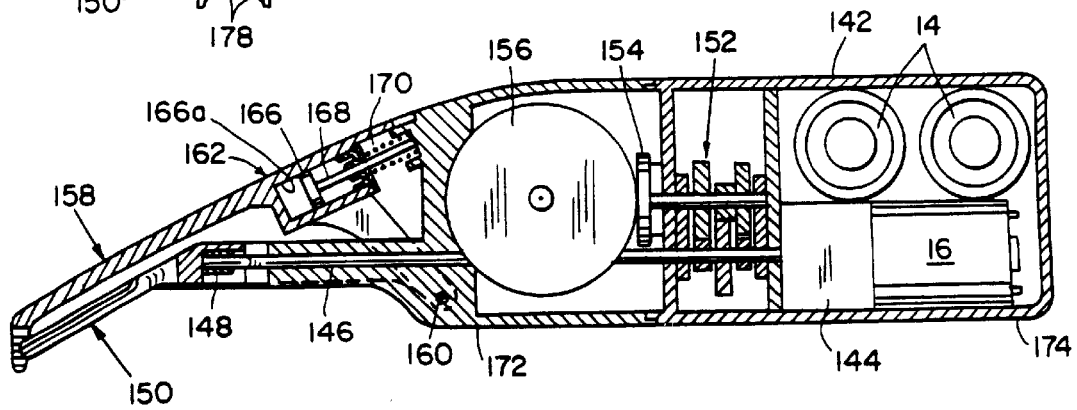
FIG. 10 is a side view, in section, of the dental cleaner of FIG. 8.

Extending downward from cantilever 114 is a thrust receiver 126. A front side of the thrust receiver includes a nodule which is received in the end portion of a compression spring 128 (FIG. 2). The opposite end of the spring is fixed to housing 12. A rear side of the thrust receiver is indented to receive an L-shaped front end portion of a push rod 130 (FIG. 2, 6 and 7). Rod 130 is slidably supported for longitudinal reciprocating movement by guides molded onto the floor of housing 12. Cantilever 114 and thrust receiver 126 are molded together with the BB fork 100 as a one piece unit.

A cam 131 is coaxially fixed to axle 22 (FIGS. 2 and 3). The cam engages a roller 132 which is rotatably supported by a pin on a cam follower 134. The follower 134 is supported for longitudinal reciprocating movement as the cam is driven by motor 16. A front end of the follower 134 engages a rear end of push rod 130. When motor 16 is energized, cam follower 134, rod 130, and the BB fork, are cyclically moved forward by cam 131. Spring 128 returns them back after each forward motion. Hence, the brushes all reciprocate forward and back.

When cleaning teeth, the brushes engage and scrub three dental surfaces simultaneously; the lingual, buccal, and top surfaces. The flexible BB fork tines allow the fork to adjust to teeth of various sizes so that all three brushes are engaged with teeth. Brushing and flossing are achieved at the same time.

The BB fork 100 also inhibits lateral motion of the front end of the dental cleaner. This is especially important when the floss encounters tight interdental gaps. As described hereinbefore, under the Flossing Fork System heading, the floss span 51 can "saw" its way through tight interdental gaps. To prevent the floss from getting caught in these gaps, the BB fork 100 braces the front end of the dental cleaner on the teeth being flossed. The added leverage overcomes tight gap resistance.

Damage to gingival tissue occurs often in hand flossing when the floss is snapped through a tight spot between teeth and motion continues until stopped by impact with the gingival tissue between the teeth. This damage can be serious especially if done repeatedly which it often is because of the poor control over the floss span in most situations. Commercially available flossing aids including motorized devices can actually make the problem worse by causing the operator to force the floss through the tight areas with force of the hand but at a greater distance from the resistance so that the ability to control the floss precisely is reduced. A major feature of the present invention is a mechanism that aids floss control and prevents damage to gingival tissue caused by excessive force pushing the floss span into the tissue.

In the present invention, the BB fork 100 in concert with the damper 120d prevent sudden floss-thrusts against gums. Upon entry of the floss span 51 into an interdental gap, the BB fork brush 112 engages an adjacent tooth and the BB fork 100 begins to pivot about pin 60. As the BB fork 100 pivots, cantilever 114 pivots damper hook 116 wherein its damper lever 118 pushes the damper piston 120. Rapid pivotal motion is thus dampened so that rapid vertical thrusts into interdental spaces are prevented. Access of the floss to the full depth of interdental spaces is allowed at a safe insertion rate.

Other additional features of dental cleaner 10 are now described. Dental cleaner 10 is designed to be disassembled by the user into two sections; a front section 130a (FIG. 2) and a rear of back section 132a. Means for quick detachment and reassembly of the two sections include a conventional latch 135 and a separable hook hinge 136.

When the two sections 130a and 132a separate, drive shaft 32R, platen 88, cam follower 134, and the damper 120d disengage from components in the front section 130a to remain with the back section 132a. The motor 16, batteries 14, and drive transmissions also remain in the back section 132a. Forks 44, 100 and spools 96S, 96T stay with the front section 130a. Separation of the two sections 130a and 132a exposes the spools 96S and 96T so the floss supply spool 96S can be replaced by a new one. A fully-loaded take-up spool 96T can be discarded and the empty supply spool can be used as a new take-up spool.

To reassemble the two sections 130a and 132a, the hinge 136 is hooked together first. The sections 130a and 132a are then pushed together and latch 135 is closed. Closing the sections 130a and 132a together engages all the drive systems. Spring 92 is tensioned by the pressure of platen shaft 84 as the platen engages the disks.

For hygienic reasons, the invention may be sold with multiple front sections 130a, each for a household user. The more costly back section 132a does not enter the oral cavity and can be shared by all household users.

Referring to FIGS. 8–11, dental cleaner 140 is another preferred embodiment of the present invention. Dental cleaner 140 includes features that function in a similar manner as those of dental cleaner 10. Dental cleaner 140 has a hollow housing 142 containing batteries 14 for energizing a motor 16. The motor drives a transmission 144 for rotating a drive shaft 146. A front end portion of the drive shaft includes a crank having a roller 148 which engages and drives a flossing fork 150 in an orbital path.

Transmission 144 also drives a platen drive transmission 152 which, in turn, drives a platen 154. A pair of floss spools 156, mated with disks, are driven by the platen in the same manner as in dental cleaner 10.

The dental cleaner 140 also includes a bracing fork 158 for bracing the dental cleaner 140 on teeth being flossed by the flossing fork 150. Both forks 150, 158 are movably connected to housing 142 by a fork pin 160.

A notable difference between dental cleaner 140 and dental cleaner 10 is the location of the bracing fork dashpot or damper 162 on dental cleaner 140. The damper cylinder 166a is molded in unison with the trunk of the bracing fork 150. A damper piston 166 is fixed to a piston rod 168 having an end which engages housing 142. Piston 166 moves within the damper 162 when the bracing fork 158 pivots about pin 160. Hence, the function of the damper 162 is the same as the damper in dental cleaner 10. The bracing fork 158 is urged back to its initial operation position by a compression spring 170 positioned between the damper 162 and housing 142. When the front section 172 of housing 142 is detached from the back section 174, the damper 162 stays with the front section 172.

Another difference between dental cleaner 140 and dental cleaner 10 is that the bracing fork 158 of dental cleaner 140 is without brush bristles. The tines 178 (FIG. 11) of the fork are bracing tines for bracing the dental cleaner 140 on a tooth. Edges of the tines 178 brace the dental cleaner on a tooth and are serrated for gripping thereon. To straddle and brace teeth of various types and sizes, the bracing tines 178 diverge with increasing distance from each other as the distance toward their distal ends increases.

Figure 12:
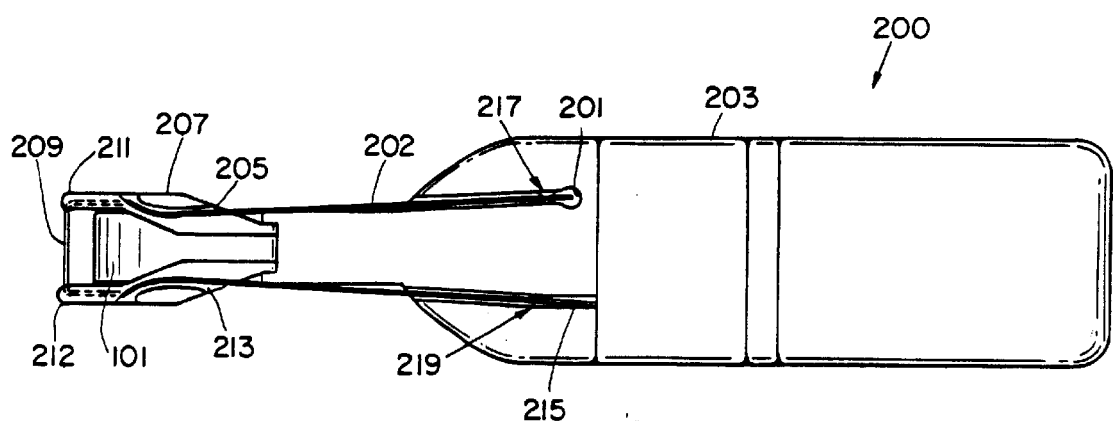
FIG. 12 is a top view of still another preferred dental cleaner.
Figure 15:
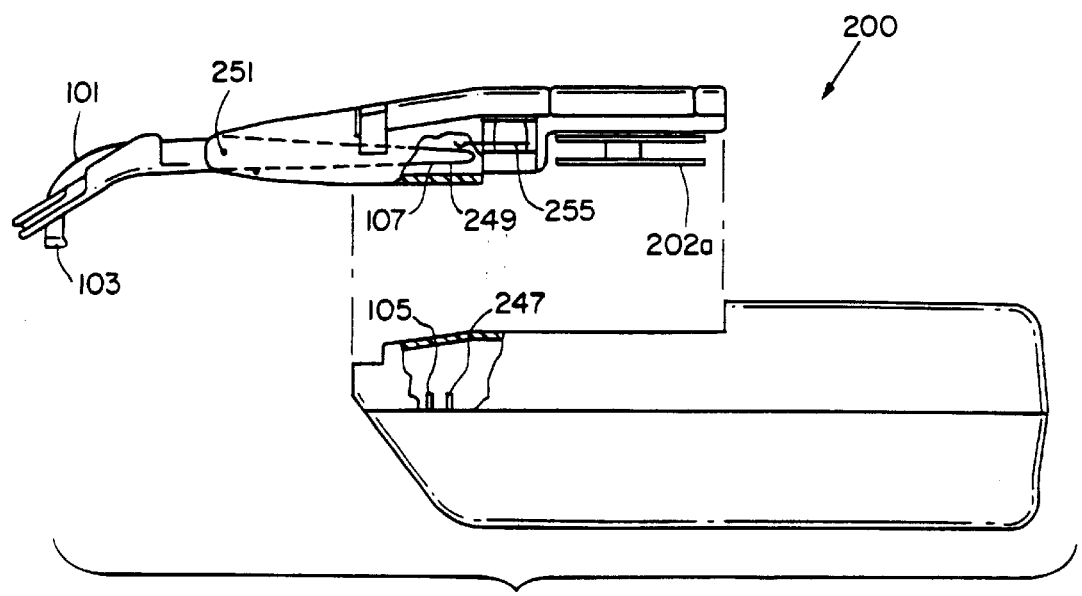
FIG. 15 is a side view of the dental cleaner depicted in FIG. 12 with the fork assembly separated from the body assembly.
Figure 16:
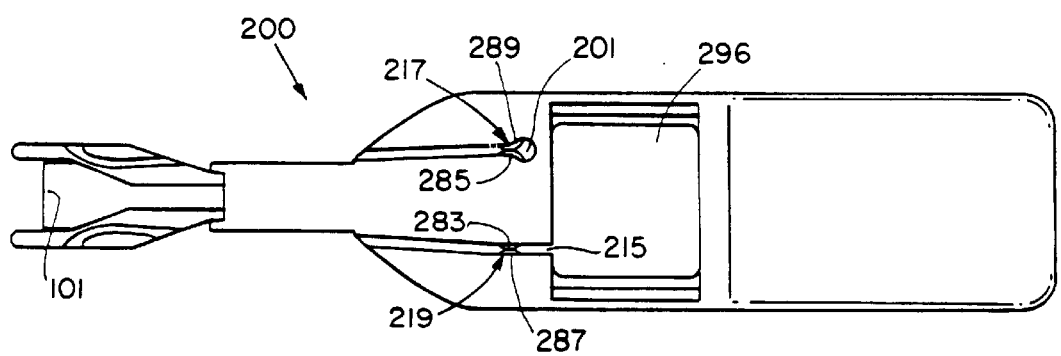
FIG. 16 is a top view of the dental cleaner depicted in FIG. 12 with the top cover removed to show the compartment for collecting used dental floss.
Figure 17:
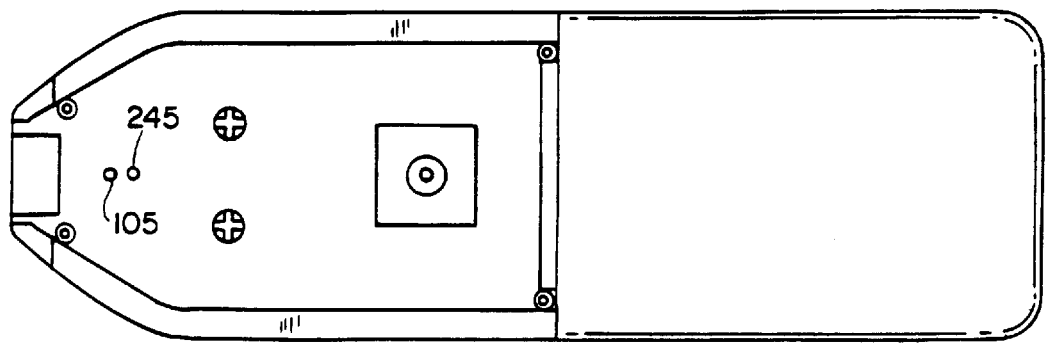
FIG. 17 is a top view of the body assembly of FIG. 15.

FIGS. 12–23 depict still another preferred embodiment of the present invention. Dental cleaner 200 extends floss 202 (FIGS. 12 and 13) from a supply spool 202a (FIG. 15) through a supply port 201 (FIG. 12) in body 203, through channel 205 in floss fork 207, across the tines 211 and 212 of floss fork 207, through channel 213 and through return port 215 into used floss storage compartment 296 (FIG. 16). This forms a span 209 of dental floss across tines 211 and 212 (FIG. 12). A pair of supply rollers 217 hold floss 202 in tension against a pair of return rollers 219.

Figure 13:
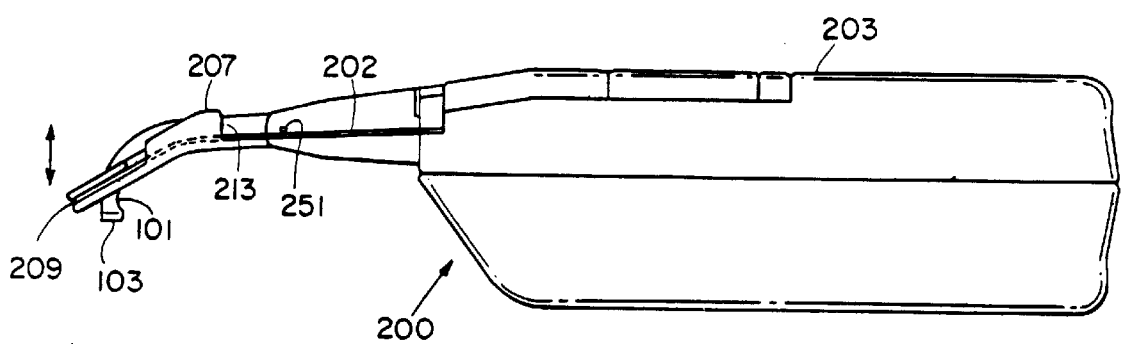
FIG. 13 is a side view of the dental cleaner depicted in FIG. 12.
Figure 14:
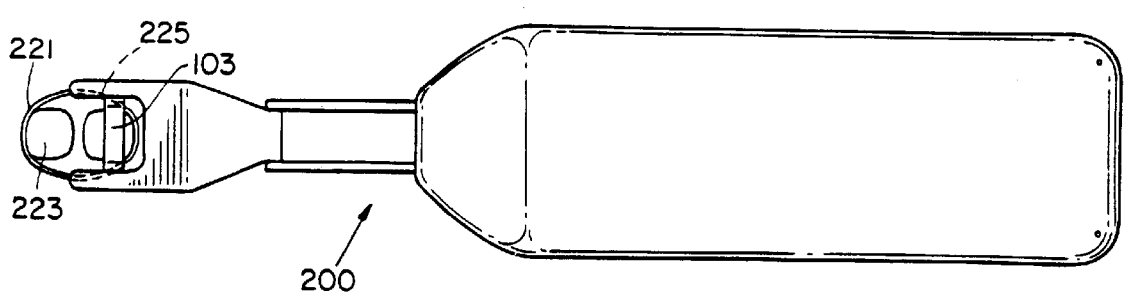
FIG. 14 is a bottom view of the dental cleaner depicted in FIG. 12.

In operation, the tines of floss fork 207 can reciprocate vertically as seen in FIG. 13 for vertical movement of floss span 209. The supply rollers 217 and return rollers 219 grip the floss 202 by pinching it between the pairs of rollers and provide longitudinal movement of floss span 209. The floss 202 (including the floss span 209) can travel in one direction a fixed distance then travel in the opposite direction a fixed distance to longitudinally oscillate the floss span. The oscillation is unbalanced such that the floss moving from the supply rollers 217 to the return rollers 219 travels a greater distance than when the floss moves from the return rollers 219 to supply rollers 217. This results in a net translation of the floss 202 from tine 211 to tine 212. As a result, the floss 202 in span 209 is continuously renewed.

Cleaning below the gum line requires forming a loop 221 (FIG. 14) in the span 209 of floss around a tooth 223. A loop 225 can also be formed in the span 209 of floss in the opposite direction. Forming either loop 221 or 225 requires pulling more floss 202 from the supply rollers 217. The drive of dental cleaner 200 allows such loops to be formed. Additionally, changing from a loop of floss to a straight span requires rapid take up of the slack dental floss. This is also accommodated by the drive of dental cleaner 200. When the span 209 is being inserted into a gap between teeth that is small and provides resistance to the floss, it is desirable to "saw" the floss through the tight region of the gap using only the longitudinal motion of the floss in span 209. This means the vertical motion of floss fork 207 must stop and only the motion provided by drive roller pairs 217 and 219 will continue. The same condition exists upon removal of the span 209 through the same tight area.

Figure 18:
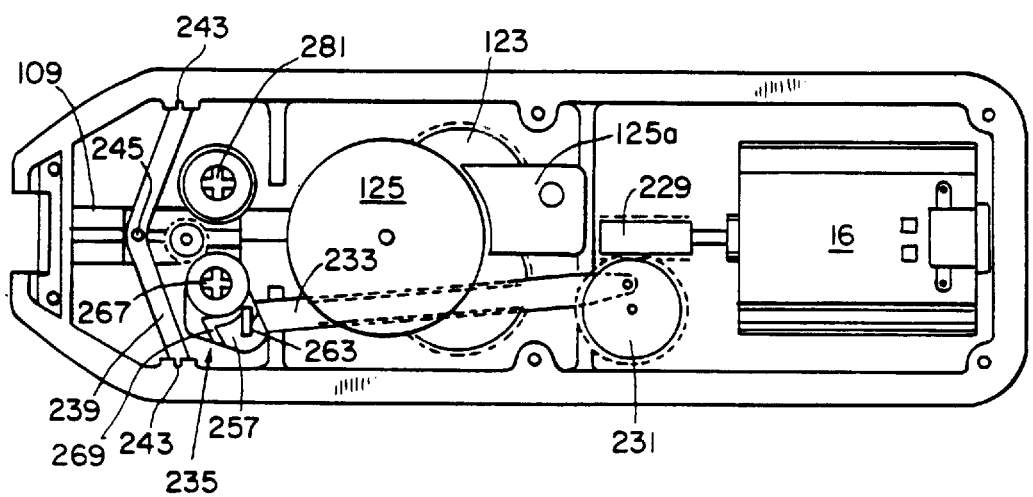
FIG. 18 is a top sectional view of the body assembly of FIG. 17 showing the drive linkage.
Figure 19:
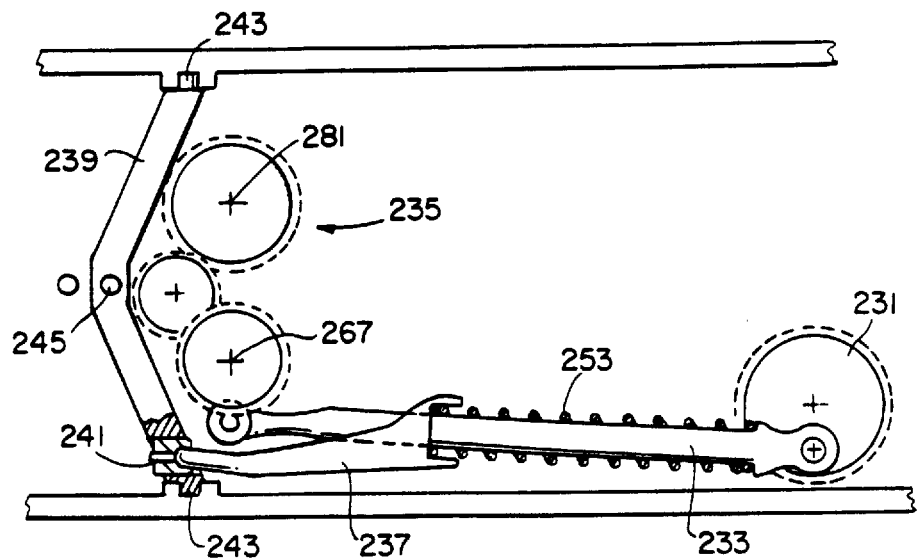
FIG. 19 is an enlarged view of the drive linkage depicted in FIG. 18.
Figure 20:
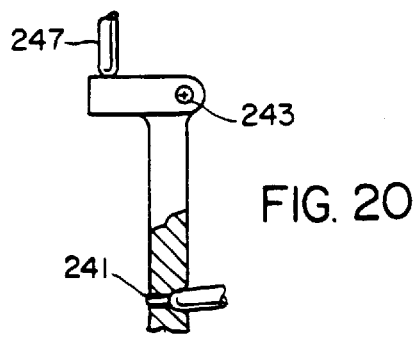
FIG. 20 is an enlarged side view of link 239.

The floss supply rollers 217, floss return rollers 219 and floss fork 207 are driven by an electric motor 16 (FIG. 18). A worm 229 is coupled to the output shaft of motor 16 for driving a worm gear 231. Connecting rod 233 is coupled to worm gear 231 for driving transmission 235. The reciprocating action of rod 233 drives link 237 (FIG. 19) which engages link 239 via ball joint 241 and oscillates link 239 about pivots 243 creating a reciprocating motion at point 245. This drives pin 247 (FIG. 20) which engages floss fork 207 at point 249 (FIG. 15) and oscillates floss fork 207 about pin 251 (FIG. 13) to provide vertical movement of floss span 209.

A spring 253 (FIG. 19) disposed about rod 233 and contacting link 237 limits the force that can be applied to the floss fork 207 so that reciprocating motion of floss fork 207 will stop when the lateral force on floss span 209 exceeds a fixed amount. Floss fork 207 is driven only on the forward stroke with the return stroke being provided by a return spring 255 (FIG. 15). The force exerted by spring 253 must be sufficient to overcome the force of return spring 255 as well as the preset load that can be applied to the floss span 209.

Figure 21:
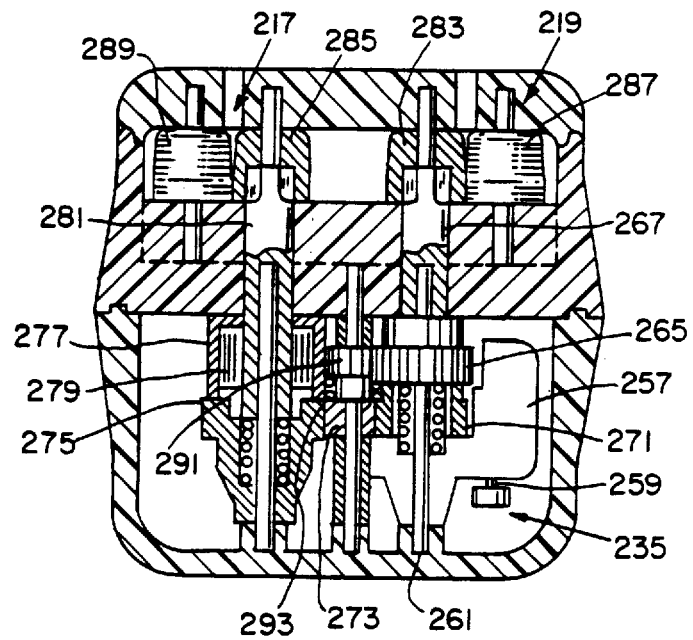
FIG. 21 is a cross-sectional view of the body assembly of FIG. 15 showing the transmission assembly.
Figure 22:
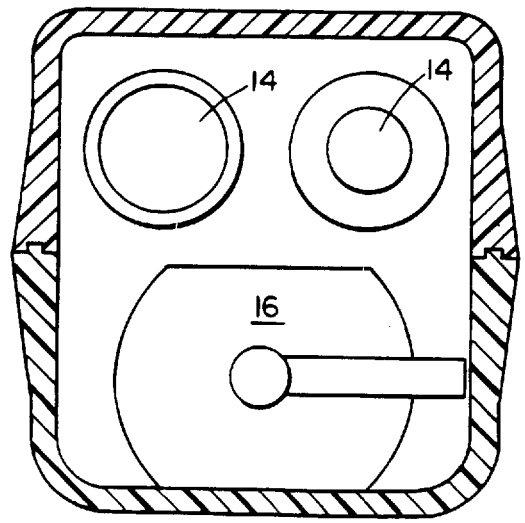
FIG. 22 is a cross-sectional view of the body assembly of FIG. 15 showing the motor and batteries.

Transmission 235 (FIG. 21) drives supply rollers 217 and return rollers 219. Transmission 235 has 5 gears, two rachet drives and 2 clutches on three parallel shafts. Rod 233 (FIGS. 18 and 19) drives rachet assembly 257 via pin 259 (FIG. 21) so that rachet assembly 257 reciprocates in approximately a 90° arc about shaft 261. When rotating in a counter clockwise direction as viewed from above (FIG. 18) rachet pawl 263 rotates gear 265 (FIG. 21) to drive roller shaft 267 counter clockwise approximately 90°. When rotating in a clockwise direction rachet pawl 269 (FIG. 18) engages gear 271 (FIG. 21). Gear 271 drives gear 273 which drives gear 275 in a clockwise direction. Gear 275 drives housing 277 which engages the OD of spring 279 winding spring 279 to create a torque on shaft 281 which engages the inner coil of spring 279. Spring 279 and housing 277 form a spring clutch. This reciprocates the active floss drive rollers 285 and 283 of supply rollers 217 and return rollers 219, respectively. The passive rollers 289 and 287 of supply rollers 217 and return rollers 219 are driven by the active rollers preferably via meshed gear teeth on the rollers or alternatively by friction. The floss 202 is driven by the friction created by being squeezed between the rollers 217 and 219.

When the floss 202 is pulled by one set of rollers, the other set provides resistance to generate tension in the floss 202. When roller 283 is driven in the counter clockwise direction pulling the floss 202, roller 285 provides the resistance. As the floss 202 is pulled against roller 285, shaft 281 turns winding spring 279 to create a torque in housing 277 and gear 275. Gear 275 drives gear 271 through gear 273 at approximately 1.3 times the speed of gear 275. Gear 271 can only go the same speed as the rachet pawl that engages it and thus the same speed as gear 265 and roller 283. In the attempt of gear 275 to overdrive gear 271, a resistance is created in the movement of gear 275 which creates a torque through spring 279 on shaft 281 and roller 285. Thus, moving floss 202 in the forward direction (counter clockwise at roller 283) winds spring 279. Spring 279 can slip relative to housing 277 if it is wound beyond a preset torque. This assures a tension in the floss 202 and allows the floss 202 to be pulled out at will at a tension that causes the spring clutch (spring 279 and housing 277) to slip.

When roller 285 is driven clockwise to pull the floss in the reverse direction, roller 283 provides the resistance that maintains the floss tension. The floss tension drives roller 283 clockwise which drives gear 265 clockwise via shaft 267. Gear 265 drives gear 291. Gear 273 is driven in this mode by gear 271. Gear 265 is larger than gear 271 and gear 291 is smaller than gear 273. Gear 291 and gear 273 are connected via spring 293. When gear 291 attempts to drive gear 273 counter clockwise, spring 293, held at one end by gear 273, wraps tightly around a cylindrical section of gear 291 to lock gear 291 to gear 273. Thus, when gear 265 driven by the floss attempts to drive gear 291 faster than gear 271 is driving gear 273, a resistance is created that provides the floss tension.

When gear 265 is driven by rachet pawl 263, the spring clutch formed by gear 291, spring 293 and gear 273 slips allowing gear 291 to rotate freely relative to gear 273 to allow free motion of gear 265.

The floss 202 is typically advanced 0.2 inches forward and 0.15 inches backward on each stroke at a frequency of about 2 strokes per second. Transmission 235 is not only capable of reciprocating the floss but is also capable of taking up slack floss and allowing floss to be pulled slack due to springs 279 and 293.

Figure 23:
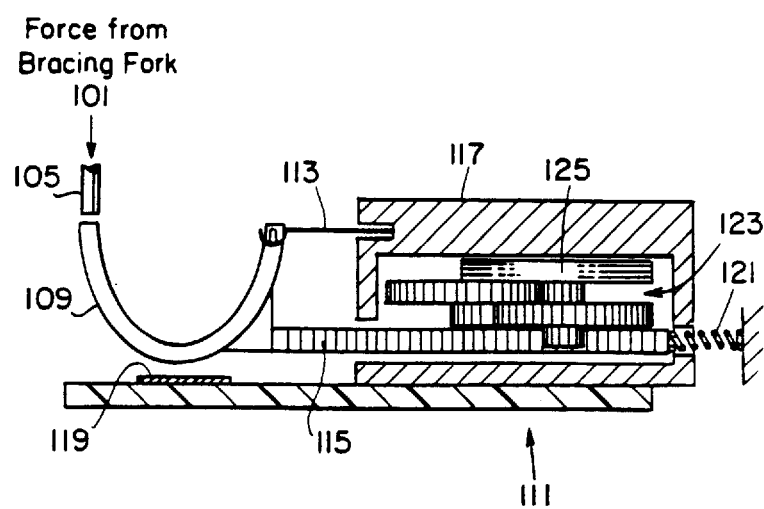
FIG. 23 is a side sectional view of the inertial damping system for the dental cleaner of FIG. 12.

Dental cleaner 200 also includes a bracing fork 101 (FIGS. 12, 13, 15 and 16) which has a generally V-shaped end 103 which rides on the teeth adjacent to the gap engaged by the floss. The bracing fork 101 pivots about pin 251 and in operation is spring loaded to maintain the V-shaped end 103 firmly on the teeth. This prevents motion of the end of dental cleaner 200 that would otherwise occur as a reaction to the forces exerted by the teeth on the floss span 209 especially when the span 209 is sawing through a tight spot. The other end of bracing fork 101 engages pin 105 at area 107 (FIG. 15). Pin 105 transfers upward forces (as viewed in FIGS. 13–15) exerted on the end of V-shaped end 103 to downward forces on lever 109 of inertial damping system 111 (FIG. 23).

Motion of the bracing fork 101 relative to body of dental cleaner 200 and floss fork 207 is regulated by inertial damping system 111. Inertial damping system 111 provides inertial resistance to the movement of bracing fork 101 in normal operation and if bracing fork 101 is excessively loaded at V shaped end 103, the resultant motion will be limited, which limits the speed with which the floss fork 207 can drive floss span 209 between teeth and into the gum. The system also adds a feel of stability to dental cleaner 200 in operation.

Lever 109 is held in position by spring 113 and rack 115. Spring 113 is fixed in gear housing 117 at one end and lever 109 is pivotably attached at the opposite end. One end of rack 115 is in contact with lever 109 and prevents free rotation of lever 109. Lever 109 is normally held above friction pad 119 by spring 113. A downward force below a preset limit exerted by pin 105 will cause rotation of lever 109 about the end of spring 113 causing rack 115 to move to the right. Rack 115 is forced to the left by spring 121 to maintain the position of lever 109 and in turn bracing fork 101. Rack 115 is meshed with a gear train 123 which amplifies the motion of rack 115 and rotates mass 125 when rack 115 is moved to the right. A clutch disengages rack 115 from mass 125 when rack 115 moves to the left. A brake 125a (FIG. 18) can be included to brake mass 125. By this mechanism, a force on rack 115 to the right rotationally accelerates mass 125, thereby providing damped resistance. A downward force above a preset limit on lever 109 will exert a force on rack 115 that will be met by an equal resistance delaying the rotation of lever 109 about the end of spring 113. This causes lever 109 to be forced downward with sufficient force to bend spring 113 and allow the midsection of lever 109 to be driven into friction pad 119, thereby, severely limiting or stopping the motion of lever 109 and in turn bracing fork 101. Stopping the motion of bracing fork 101 stops the movement of the entire dental cleaner 200 relative to the teeth and this prevents floss fork 207 from driving floss span 209 into the gum. Therefore, by this mechanism, when floss span 209 is being forced between teeth and suddenly slips free, the force is immediately transferred to the bracing fork 101, which will resist the force and lock up if the force is excessive, preventing floss span 209 from being driven into the gum. Yet, when the motion is halted and the force reduced, the floss span 209 can be guided under the gum line because the bracing fork will be free to move.

Figure 24:
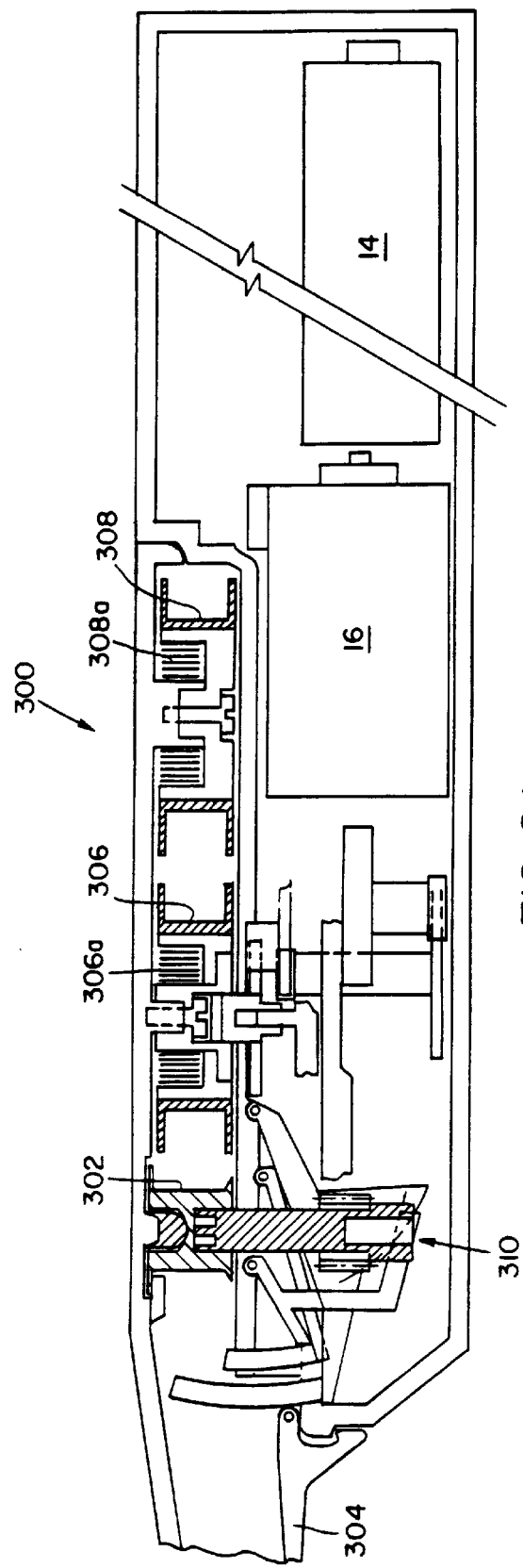
FIG. 24 is a side sectional view of another preferred dental cleaner.

FIG. 24 depicts another preferred embodiment of the present invention. Dental cleaner 300 is similar to dental cleaner 200 differing mainly in that the floss 202 is driven by two capstans 302, one for supplying floss and another for returning floss rather than by two pairs of pinch rollers. Sufficient friction between the capstans and the floss 202 for driving the floss 202 is provided by wrapping the floss 202 around each capstan 302 two turns. The supply and return spools 308 and 306 are located in line with each other. Floss fork 304 is driven by drive 310. Drive 310 is functionally similar to the drive that drives floss fork 207 of dental cleaner 200.

Figure 25:
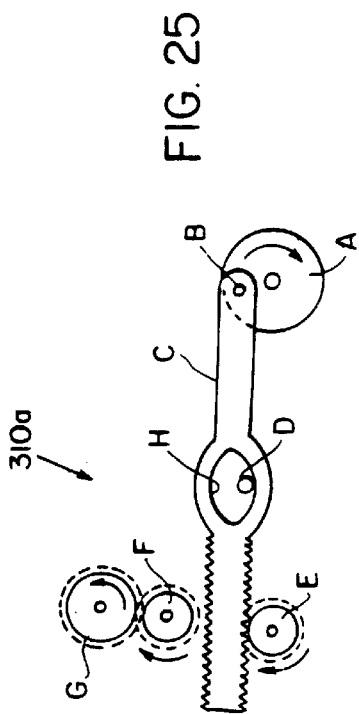
FIG. 25 is a simplified drawing of a portion of the drive for the dental cleaner of FIG. 24.
Figure 26:
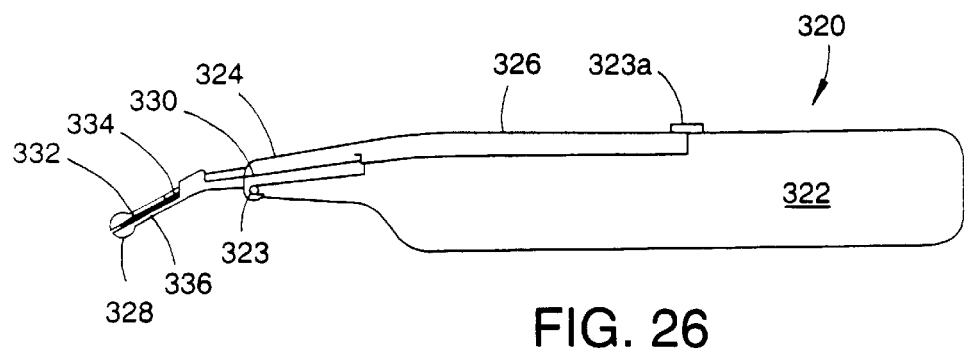
FIG. 26 is a side view of another preferred dental cleaner.
Figure 27:
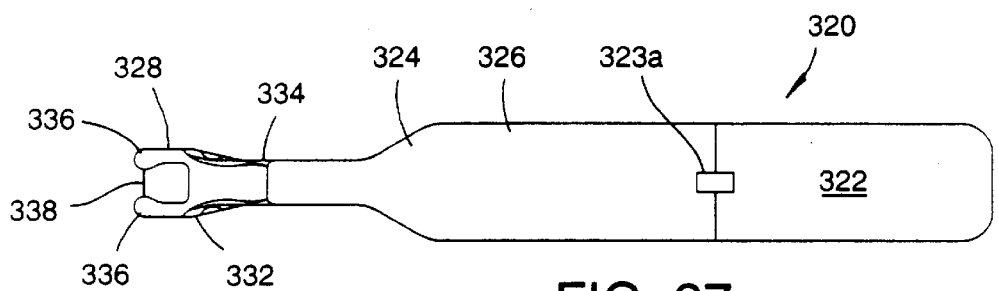
FIG. 27 is a top view of the dental cleaner of FIG. 26.
Figure 28:
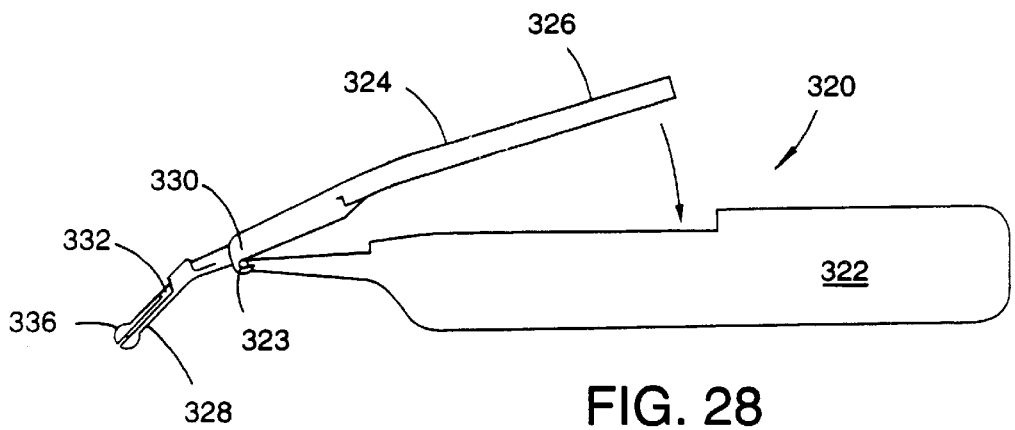
FIG. 28 is a side view of the dental cleaner of FIG. 26 showing the detachable subassembly partly separated from the main assembly.

Referring to FIG. 25, drive 310a is another preferred drive which can be employed instead of drive 310 to drive capstans 302. Gear A is driven in a clockwise direction by the motor through a gear reduction such as a worm gear. Rack C is coupled to gear A by pin B at a location offset from the center of rotation of gear A, thereby forming a crank to drive rack C. Gear A drives rack C in an orbital motion guided by pin D and the interactions with gear E and F. Gears E and G drive capstans 302 via connecting shafts. Gear F reverses the motion imparted by rack C to obtain the correct motion of Gear G. Hole H in rack C is shaped to alternatively engage rack C to gear E and gear F.

In the position shown in FIG. 25, gear A is driving rack C to the right and rack C is held engaged to gear E by pin B and pin D in conjunction with shaped hole H which acts as a cam surface. Gear E rotates clockwise and will continue to be rotated clockwise until rack C is pulled as far right as possible. At that point, the left side of hole H will engage pin D and as gear A continues to rotate moving pin B downward, rack C will rotate about pin D so that gear F is engaged. As gear A continues to further rotate, rack C is driven to the left and rotates gear F clockwise which in turn rotates gear G counter-clockwise. When pin B is in its extreme left position, the right side of hole H engages pin D and rack C is moved back into engagement with gear E.

Gear E drives the return capstan and gear G drives the supply capstan. Gear G is larger than gear E and, therefore, rotates fewer degrees than gear E. Thus, the floss is driven further in the return direction than the supply direction so that for each cycle of motion, a net movement results from supply to return.

An important feature of this transmission is that when one gear is driven, the other is free to rotate. When gear E is driving the return capstan, the supply capstan driven by gear G is free to rotate to allow floss to be pulled directly from the supply spool 308 (FIG. 24). The rotation of the supply spool 308 is restricted by a clutch and power spring 308a. The action of the floss pulling on the spool 308 rotates the spool against the resistance of the power spring and winds the power spring until the clutch begins to slip. By this means, a tension is maintained on the floss 202 as the floss is pulled by the return capstan. If a loop of floss is pulled and released, the spring first unwinds, then rewinds to quickly return tension to the floss. Maintenance of tension is not only important during the forward motion of the floss but also for the return motion. When the supply capstan is rotating in reverse and feeding floss back to the supply spool, tension is required between the spool and capstan to maintain the frictional grip between the capstan and the floss. When the capstan is rotated in reverse, the spool is rotated by the power spring to maintain the required tension.

The return spool 306 must maintain tension on the floss between the return spool and the return capstan. The return spool 306 is driven by the motor through a gear reduction. A power spring and clutch 306a are between the spool and shaft that is driven by the motor. The driving shaft winds the spring until the clutch slips so that a tension is maintained even though the forward motion of the capstan may momentarily exceed the driving speed of the spool. Tension is also maintained when the return capstan drive is disengaged as the supply capstan is being driven. If a loop is pulled in the floss, the spring will quickly take up the slack and restore tension when the supply capstan is being driven.

FIGS. 26–31 depict another preferred dental cleaner indicated by reference numeral 320. The dental cleaner 320 is comprised of a main body or main assembly 322 and a subassembly 324. The subassembly 324 is detachably connectable to the main assembly 322 for expedient replacement of the subassembly 324 by a user. Connecting means for the two assemblies include an anteriorly positioned detachable hinge 323, and a posteriorly positioned conventional latch 323a. Interfaces are provided with conventional water-resistant seals (not shown).

A plurality of systems operate various working features of dental cleaner 320. For organization and clarity, each system is separately described hereinafter.

The first system of dental cleaner 320 to be described is the subassembly floss route and guide system. The subassembly 324 (FIGS. 26–28) includes a frame or housing 326. A floss fork 328 is pivotally supported on the housing 326 by a pin 330. Guide grooves 332 (FIG. 29) on the fork 328 guide the movement and transfer of dental floss 334 from one tine 336 to the other tine 336 so that the floss 334 forms a movable floss span 338 between the tines 336.

Figure 29:
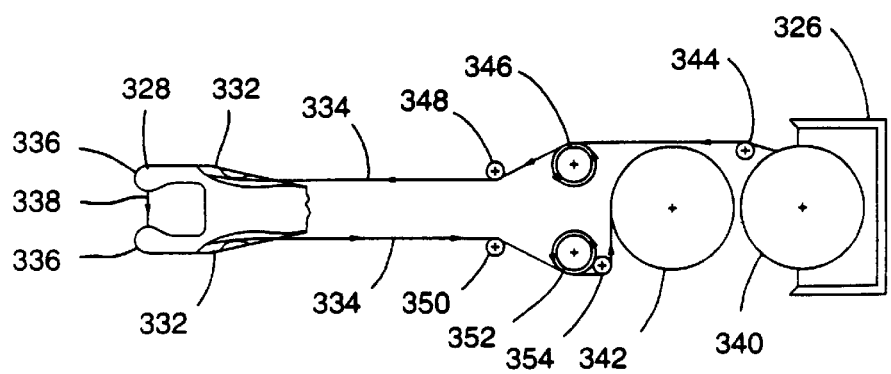
FIG. 29 is a top, partly diagrammatic, view of a floss route and guide system within the subassembly of the dental cleaner of FIG. 28.

Also included is a floss supply spool 340 and a floss take-up spool 342 (FIG. 29). Clean floss 334 drawn from supply spool 340 engages a guide roller 344, wraps around a reverse capstan 346, engages a guide roller 348, and then passes though the guide grooves 332 of fork 328 to form the floss span 338. Used floss 334 returning from the fork 328 engages a guide roller 350, wraps around a forward capstan 352, engages a guide roller 354 and is wound onto take-up spool 342. The driving surfaces of the capstans are lined with a high-friction rubber to maintain proper driving friction under varying operational conditions. The shafts for supply spool 340, take-up spool 342, guide roller 344, reverse capstan 346, guide roller 348, guide roller 350, forward capstan 352 and guide roller 354 are parallel to each other. This allows subassembly 324 to be easily attached to and detached from the main body 322.

The floss 334 is reciprocated longitudinally along the floss span 338 by driving the capstans 346 and 352 alternately in order to reverse the direction of motion of the floss span 338 alternately. The forward capstan 352 advances the floss 334 forward, then the reverse capstan 346 reverses the floss direction. The forward motion of the floss 334 is slightly greater than the reverse motion to result in a net transfer of floss 334 from the supply spool 340 to the take-up spool 342. A vertical or up and down motion is also imparted to the floss span 338 by an up and down pivotal motion of the fork 328 as explained later in the description of the fork drive system.

Loading the floss spools and threading the floss route in the subassembly 324 may be done at the factory wherein the subassembly 324 may be sold as a disposable cartridge. The floss supply in the cartridge is expected to last about three months if used by an individual once a day.

Figure 30:
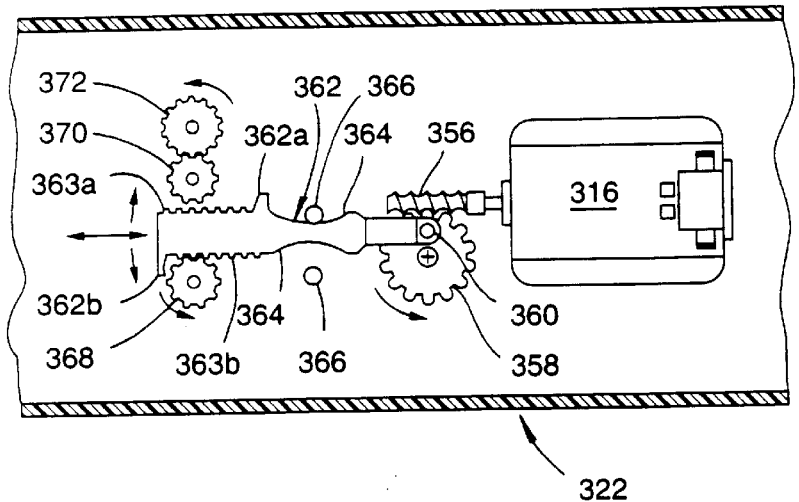
FIG. 30 is an expanded fragmental sectional view showing the capstan drive system within the main assembly of the dental cleaner of FIG. 28.

The capstan drive system of dental cleaner 320 is shown in FIG. 30 and described as follows. The capstan drive system is similar to drive 310a (FIG. 25). Housed within the hollow main body 322 of the dental cleaner 320 is an electric motor 316 which drives a worm 356. The worm 356 is drivingly engaged with a worm gear 358 having an eccentrically positioned pin 360. A bore through an end portion of a movably supported drive arm or rack 362 receives the pin 360 for rotation therein and forms a crank for driving drive rack 362.

Rack 362 is double-sided with two rows of teeth 363a and 363b. which are on opposite sides of rack 362. The rack 362 also includes two symmetrical cams 64 next to teeth 363a and 363b. Two guide pins 366, having end portions fixed in a wall of the main body 322, are positioned on opposite sides of rack 362 to be alternately engaged by the cams 364. When the rack 362 is driven by worm gear 358, pins 366 guide the rack 362 to alternately engage teeth 362b with a forward capstan gear 368 and teeth 362a with an intermediate gear 370 which is engaged with a reverse capstan gear 372. Rack 362 includes two protrusions 362a and 362b which are positioned at opposing ends of teeth 363a and 363b, respectively. If intermediate gear 370 is not in the proper orientation for engaging teeth 363a of rack 362, protrusion 362a will engage and move intermediate gear 370 into the proper orientation for engagement. Additionally, if forward capstan gear 368 is not in the proper orientation for engaging teeth 363b of rack 362, protrusion 362b will engage and move forward capstan gear 368 into the proper orientation for engagement. If intermediate gear 370 and forward capstan gear 368 are already in the proper orientation for engaging respective teeth of rack 362, protrusions 362a and 362b will not move the gears.

A shaft extending from forward capstan gear 368 passes out of the main body into the subassembly 324 and is keyed to detachably insert into forward capstan 352 (FIG. 29) for driving the same. A shaft extending from reverse capstan gear 372 passes out of the main body 322 into the subassembly 324 and is keyed to detachably insert into reverse capstan 346 for driving the same. Hence, the cyclic motion of the rack 362 drives the capstans alternately to reciprocate the floss span 338 longitudinally.

The capstan gear ratios are selected to produce a greater amount of rotation of the forward capstan 352 relative to the reverse capstan 346. This results in a net transfer of floss 334 from the supply spool 340 to the take-up spool 342 with each cycle of the capstan drive system. Typically, the gear ratios are selected to advance floss 334 between about 0.010 to 0.050 inches per stroke.

The capstan gears, like most of the gears in the cleaner, are supported on shafts which are rotatably supported by bearings in the walls of the main body 322.

Figure 31:
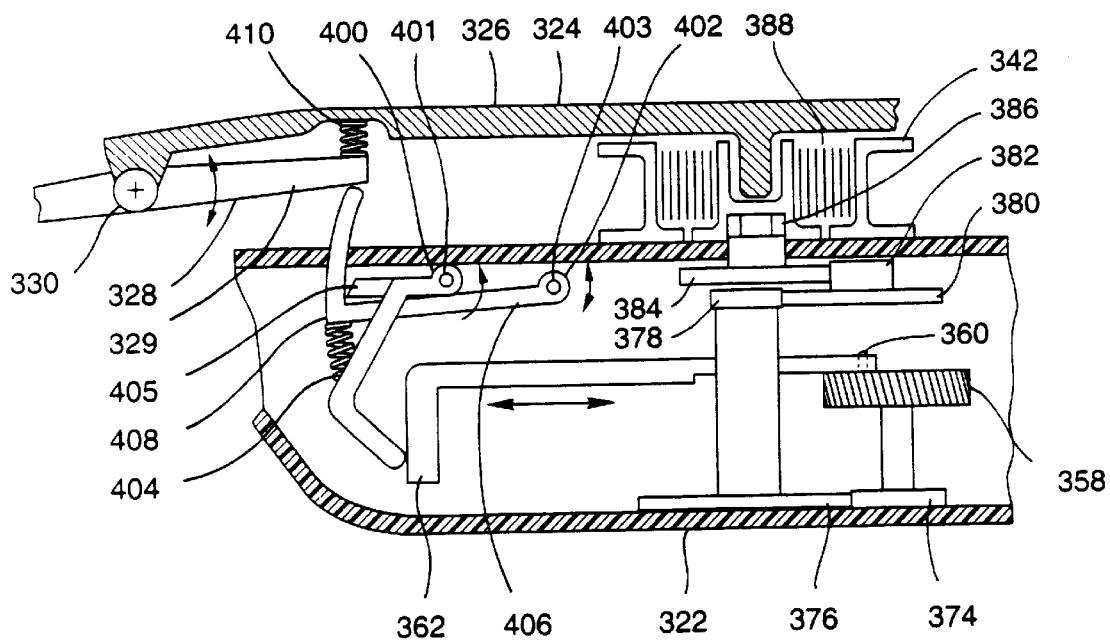
FIG. 31 is an expanded fragmental side view, partly in section, showing the fork drive system and the spool drive system within the main assembly of the dental cleaner of FIG. 28.

The spool drive system of dental cleaner 320 is shown in FIG. 31 and is described as follows. A first spool drive gear 374 is coaxially fixed on a common shaft with the worm gear 358. Gear 374 is the first gear of a speed reduction gear train for driving the take-up spool 342.

The train also includes a second gear 376, a third gear 378, a fourth gear 380, a fifth gear 382, and a sixth gear 384. The last gear 384 of the train is fixed to a drive shaft 386 which passes out of the main body 322 and into the subassembly 324. Shaft 386 is keyed to detachably insert into the take-up spool 342 within the subassembly 324 to drive the take-up spool 342.

Within the hub of the take-up spool 342 is a torsion spring 388. The inside end of the spring 388 is grounded to the drive of take-up spool 342 while the outside of the spring 388 is frictionally connected to the inner diameter of the spool hub to form a clutch. A torsion spring is also included in the hub of the supply spool 340 and is similarly connected to the latter, except that the spring inside end is grounded to the frame of the subassembly 324.

When the motor 316 is running, the spool springs wind until they slip relative to their respective spool hubs. Floss tension is set by the springs, the clutch resistance, and resistance encountered in the floss route.

The springs enable floss to be drawn from the spools to form a loop at the ends of the fork tines, such as to floss around a tooth. A longer loop can be formed in the rare event that floss gets caught on a dental prosthetic, so the cleaner can be removed from the mouth. In all cases, when the loop is released, the springs immediately pull in the slack and wind it back on the spools wherein normal floss tension is restored. Floss 334 drawn to form a loop is taken alternately from both spools as the capstan drive system alternately shifts from driving one capstan to the other. The spool springs wind and slip at a set torque when floss 334 is pulled from the spools.

FIG. 31 also shows the fork drive system of dental cleaner 320. A posterior end portion of fork 328 forms a lever 329 which pivots the fork about pin 330. Vertical reciprocating motion (transverse to floss span 338) is produced at the anterior ends of the fork tines 336 (FIG. 26) as result of fore and aft motion of rack 362.

The motion of rack 362 is translated by a two-piece hinged lever assembly which includes a first lever 400 and a second lever 402. The levers are pivotally supported by pins 401, 403 received through bores in respective hinge end portions of the levers 400 and 402. End portions of the pins 401 and 403 are fixed in a wall of the main body 322.

A lower end portion of lever 400 abuts a distal end of rack 362. A preloaded release spring 404, positioned between a step in first lever 400 and the bottom of second lever 402, operatively connects the first 400 and second 402 levers. A spring pre-load stop 405, formed by a cantilever fixedly extending from lever 400, is positioned to engage lever 402 to maintain the spring pre-load between the levers. When operating conditions cause spring 404 to compress beyond the pre-load state, stop 405 disengages from lever 402.

Lever 402 is L-shaped comprising legs 406 and 408. Leg 408 protrudes through an aperture in the main body 322 and into the subassembly 324 to abut and drive the fork lever 329 upward. Downward motion of lever 329 is produced by a fork return spring 410 which spring-loads lever 329 against lever 402. Spring 410 is positioned between lever 329 and an upper wall of the subassembly housing 326.

In the event that the fork floss span 338 encounters greater than normal flossing resistance, such as encountering a tight interdental gap, the vertical motion of fork 328 is attenuated or stops. The cyclic motion of rack 362 is then absorbed by spring 404. While the fork 328 idles, the side-to-side motion of the floss 334 in floss span 338 continues so that the floss 334 can work its way through the tight gap. Upon getting through the gap, the vertical oscillations of fork 328 resume.

The power system of dental cleaner 320 includes rechargeable batteries and a conventional motion control electronics package (not shown) electrically connected to the motor 316 and housed in the hollow posterior of the main body 322. The system for energizing the motor 316, including an on/off switch and battery recharging means, is similar to those of conventional electric tooth brushes.

Figure 32:
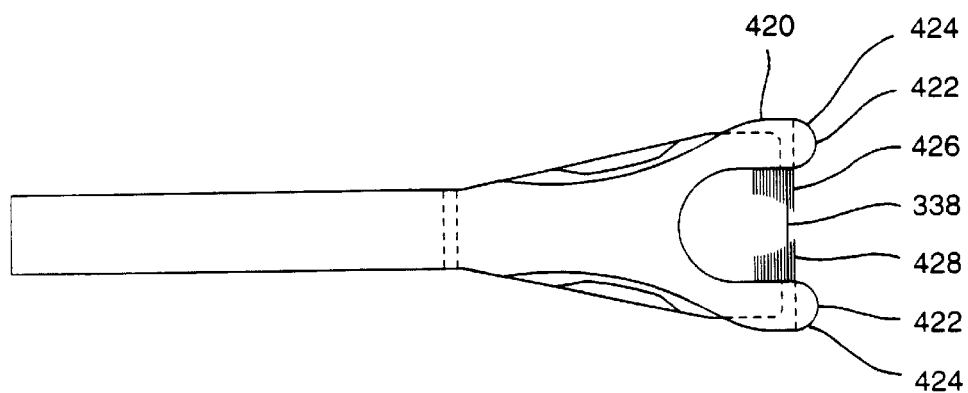
FIG. 32 is a top view of another preferred fork.
Figure 33:
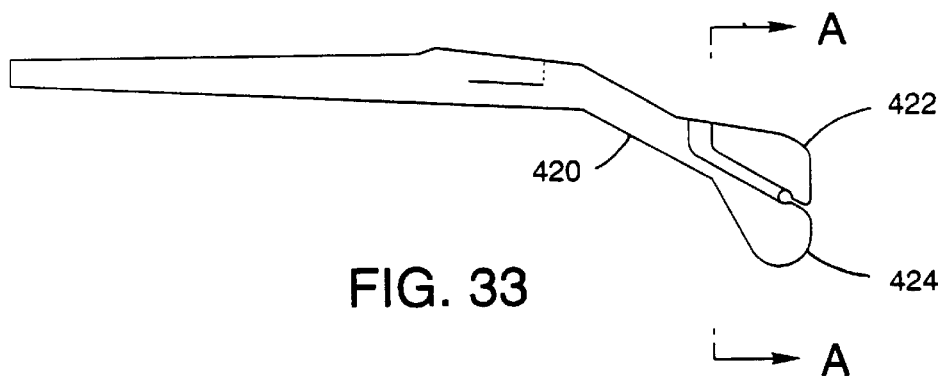
FIG. 33 is a side view of the fork of FIG. 32.
Figure 34:
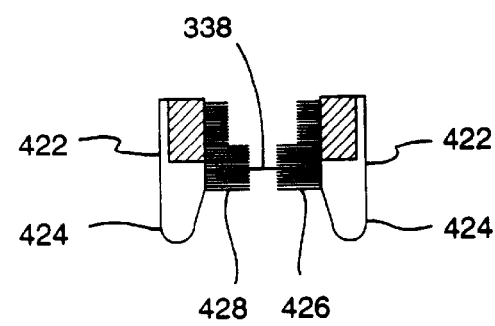
FIG. 34 is a sectional view taken along the line A—A of FIG. 32.

FIGS. 32–34 depict another preferred flossing fork 420 having tines 422 which is similar to fork 328, but includes additional features. The fork 420 can replace fork 328 on the dental cleaner 320 to be pivotally supported and driven in the same manner as fork 328.

One of the features of fork 420 is that each tine 422 has a bracing pad 424. Each bracing pad 424 has an inner surface facing the opposite bracing pad 424 which extends down and away from the opposite pad to conform to a user gum line. Thus, the bracing pads 424 together can comfortably brace on both sides of user gums to inhibit lateral motion of the fork 420 as the floss 334 of floss span 338 reciprocates between tines 422.

Fork 420 includes first and second brushes 426, 428 attached to the tines 422, respectively. The brushes 426 and 428 include bristles embedded in the plastic tines in the same manner as in toothbrushes. The bristles extend inward between the tines 422 for simultaneously engaging lingual and buccal tooth surfaces. Hence, the brushes 426 and 428 help to inhibit lateral motion of the fork 420 as the floss 324 reciprocates.

Since the fork 420 is pivotally supported on the dental cleaner 320 for being driven vertically, the brushes 426 and 428 are thereby supported to move up and down as the fork 420 reciprocates vertically. Hence, user teeth are flossed and brushed simultaneously. The brushes 426 and 428 are shaped with bristles of various lengths to engage around and between teeth.

Figure 35:
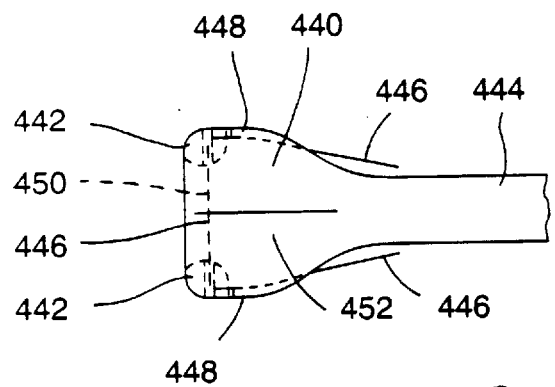
FIG. 35 is a top view of the tip of still another preferred fork.
Figure 36:
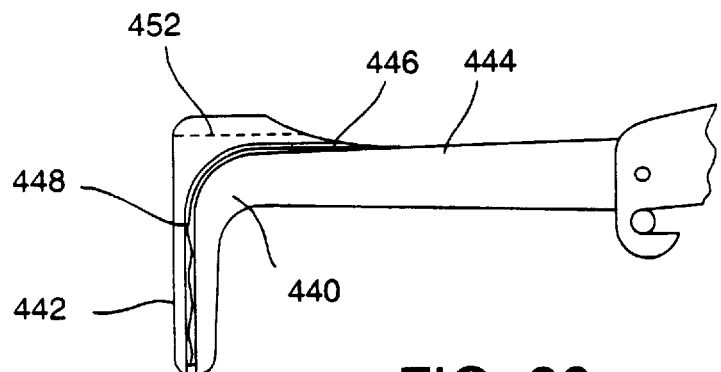
FIG. 36 is a side view of the fork of FIG. 35.
Figure 37:
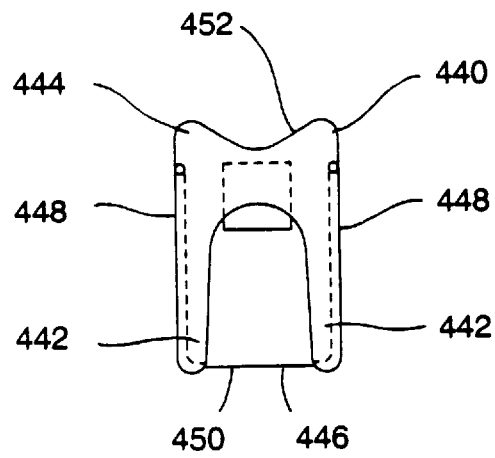
FIG. 37 is a front view of the fork of FIG. 35.

FIGS. 35–37 depict the tip 440 of still another preferred flossing fork 144 which provides a bite device for driving a span 450 of floss 446 through an interdental gap that is too tight for easy entry of floss therebetween. Tip 440 includes a pair of vertical tines 442 for supporting the span 450 of floss 446 therebetween, and floss guides 448 for guiding floss 446 to and from the tines 442. The top portion of tip 440 includes an angled groove 452 which lies along a longitudinal axis that is perpendicular to the span 450 of floss 446. By positioning his/her teeth along groove 452, a user can bite down on groove 452 to drive the span 450 of floss 446 through a tight interdental gap. The user can prevent damage to the gums by controlling the speed at which he/she bites down on groove 452. The angled configuration of groove 452 prevents the teeth of the user from slipping off tip 440 and positions the driving teeth opposite the center of span 450.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. This includes combinations of features from the different embodiments disclosed.

What is claimed is:

1. A dental cleaner comprising:
    a fork having a pair of spaced tines for supporting a floss span extending therebetween; and
    first and second brushes attached to the tines, respectively, the brushes having bristles extending inward between the tines for simultaneously engaging lingual and buccal tooth surfaces.

2. The dental cleaner as defined in claim 1 further comprising a drive for driving the floss span to floss teeth.

3. The dental cleaner as defined in claim 1 further comprising a drive for driving the brushes to brush teeth.

4. The dental cleaner as defined in claim 1 wherein the brushes have bristles of differing lengths.

5. A dental cleaner comprising:
    a subassembly including a frame supporting a pair of spaced tines, the tines for supporting a moveable floss span therebetween and having guides for guiding the transfer of dental floss from one tine to the other tine, a pair of capstans near the tines for engaging and driving floss to reciprocate the floss span between the tines, and a floss supply and take-up system for replacing the floss span; and
    a main assembly including a housing containing a drive for driving the capstans, the main assembly and the subassembly being detachably connectable to each other.

6. The dental cleaner as defined in claim 5 wherein the capstans and the floss supply and take-up system include parallel support shafts, the parallel shafts allowing the subassembly to be easily connected and disconnected from the main assembly.

7. The dental cleaner as defined in claim 5 wherein the drive reciprocates the tines transverse to the floss span.

8. The dental cleaner as defined in claim 5 wherein the subassembly is a disposable cartridge.

9. A dental cleaner comprising:
    a frame supporting a pair of spaced tines, the tines for supporting a moveable floss span there-between and having guides for guiding the transfer of dental floss from one tine to the other tine;
    a pair of capstans near the tines for engaging and driving floss to reciprocate the floss span between the tines; and a capstan drive for driving the capstans, the capstan drive including a rack which moves in a path that alternately drives each capstan.

10. The dental cleaner as defined in claim 9 wherein the rack has teeth on opposite sides so that each side of the rack drives a respective capstan.

11. The dental cleaner as defined in claim 9 wherein the rack is driven by a crank connected to the rack.

12. The dental cleaner as defined in claim 9 wherein the rack is guided by a cam.

13. The dental cleaner as defined in claim 9 further comprising a floss supply and take-up system for automatically replacing the floss span.

14. A dental cleaner comprising:

a frame supporting a pair of spaced tines, the tines for supporting a moveable floss span therebetween and having guides for guiding the transfer of dental floss from one tine to the other tine;

a drive for reciprocating the floss span between the tines to floss teeth; and a pair of bracing pads, each pad being on an inner side of a respective tine and having a surface facing the other pad which extends down and away from the other pad to conform to a user gum line thereby comfortably bracing the tine thereon when flossing.

15. A method of simultaneously flossing and brushing teeth with a dental cleaner comprising the steps of:

flossing the teeth with a span of floss supported between a pair of spaced tines of a fork; and simultaneously engaging lingual and buccal tooth surfaces of the teeth with first and second brushes attached to the tines, the brushes having bristles extending between the tines.

\* \* \* \* \*